United States Patent
Zhang

(10) Patent No.: US 10,451,551 B2
(45) Date of Patent: Oct. 22, 2019

(54) METHODS FOR HIGH-THROUGHPUT FLUORESCENCE IMAGING WITH SAMPLE HEATING CAPABILITY

(71) Applicant: OmniVision Technologies, Inc., Santa Clara, CA (US)

(72) Inventor: Bowei Zhang, Fremont, CA (US)

(73) Assignee: OmniVision Technologies, Inc., Santa Clara, CA (US)

( * ) Notice: Subject to any disclaimer, the term of this patent is extended or adjusted under 35 U.S.C. 154(b) by 172 days.

(21) Appl. No.: 15/413,045

(22) Filed: Jan. 23, 2017

(65) Prior Publication Data

US 2017/0167978 A1    Jun. 15, 2017

Related U.S. Application Data

(62) Division of application No. 14/513,985, filed on Oct. 14, 2014, now Pat. No. 9,574,991.

(51) Int. Cl.
*C12Q 1/6809*     (2018.01)
*G01N 21/64*     (2006.01)
(Continued)

(52) U.S. Cl.
CPC .... *G01N 21/6428* (2013.01); *B01L 3/502715* (2013.01); *B01L 7/525* (2013.01);
(Continued)

(58) Field of Classification Search
None
See application file for complete search history.

(56) References Cited

U.S. PATENT DOCUMENTS

| | | | |
|---|---|---|---|
| 8,380,457 B2 * | 2/2013 | Coursey | B01L 7/525 |
| | | | 702/133 |
| 2004/0120854 A1 | 6/2004 | Heath et al. | |

(Continued)

FOREIGN PATENT DOCUMENTS

| | | | |
|---|---|---|---|
| CN | 103884698 A | 6/2014 | |
| WO | WO-2005073407 A1 * | 8/2005 | ......... G01N 21/6408 |

OTHER PUBLICATIONS

Cui et al., "Lensless high-resolution on-chip optofluidic microscopes for Caenorhabditis elegans and cell imaging", PNAS, Aug., vol. 105, No. 31, pp. 10670-10675. (Year: 2008).*
Arpali, S.A. et al. High-throughput screening of large volumes of whole blood using structured illumination and fluorescent on-chip imaging; Published in final edited form as: Lab Chip. Dec. 7, 2012; 12(23): 4968-4971; 10 pages.
(Continued)

*Primary Examiner* — Young J Kim
(74) *Attorney, Agent, or Firm* — Lathrop Gage LLP

(57) ABSTRACT

A method for high-throughput assay processing includes (a) modulating temperature of a plurality of samples disposed in a respective plurality of fluidic channels on an image sensor wafer, including a plurality of image sensors, by heating the image sensor wafer using a heating module thermally coupled with the image sensor wafer, to control reaction dynamics in the samples, and (b) capturing a plurality of fluorescence images of the samples, using the plurality of image sensors, to detect one or more components of the plurality of samples. A method for manufacturing a high-throughput fluorescence imaging system with sample heating capability includes (a) bonding a fluidic wafer, including a plurality of recesses, to an image sensor wafer including a plurality of image sensors, and (b) bonding a heating module, including a heater for generating heat, to the image sensor wafer to thermally couple the heater and the image sensor wafer.

10 Claims, 12 Drawing Sheets

(51) Int. Cl.
  *G01N 21/03* (2006.01)
  *B01L 3/00* (2006.01)
  *B01L 7/00* (2006.01)
  *G01N 21/17* (2006.01)
  *G01J 3/44* (2006.01)

(52) U.S. Cl.
  CPC ....... *C12Q 1/6809* (2013.01); *G01N 21/0332* (2013.01); *G01N 21/1717* (2013.01); *G01N 21/6454* (2013.01); *G01N 21/6456* (2013.01); *B01L 2300/044* (2013.01); *B01L 2300/047* (2013.01); *B01L 2300/0803* (2013.01); *B01L 2300/0887* (2013.01); *B01L 2300/1827* (2013.01); *G01J 3/4406* (2013.01); *G01N 2021/1731* (2013.01); *G01N 2021/6419* (2013.01); *G01N 2021/6421* (2013.01); *G01N 2021/6471* (2013.01)

(56) References Cited

U.S. PATENT DOCUMENTS

2013/0231254 A1   9/2013  Kawashima et al.
2013/0307954 A1*  11/2013  Vaartstra ................ G01N 21/01
                                                          348/77

OTHER PUBLICATIONS

Han C., et al. Wide Field-of-View On-Chip Talbot Fluorescence Microscopy for Longitudinal Cell Culture Monitoring from within the Incubator; 2Anal. Chem. 2013, 8S, 2356-2360.
Taiwan Application No. 104132867, English Translation of the Office Action dated Aug. 25, 2016, 3 pages.
Taiwan Application No. 104132867, English Translation of the Seccond Office Action dated Feb. 7, 2017, 1 page.
Cui, Xiquan, et al., "Lensless High-Resolution On-Chip Optofluidic Microscopes for Caenorhabditis Elegans and Cell Imaging," PNAS, vol. 105, No. 31, pp. 10670-10675, Aug. 5, 2008.
Chinese Patent Application No. 201510662706.9 First Office Action dated Apr. 18, 2019, with English language summary, 8 pages.

* cited by examiner

METHODS FOR HIGH-THROUGHPUT FLUORESCENCE IMAGING WITH SAMPLE HEATING CAPABILITY

CROSS-REFERENCE TO RELATED APPLICATIONS

This application is a divisional application of U.S. patent application Ser. No. 14/513,985 filed Oct. 14, 2014, which is incorporated herein by reference in its entirety.

BACKGROUND

Fluorescence imaging is a commonly used technique for detecting components of a biological sample, such as a blood, urine, or saliva sample from a human or animal subject, to characterize an aspect of the sample. Sample components of interest are labeled with fluorescent tags that emit fluorescence upon excitation with light of an appropriate wavelength. Fluorescence imaging is used to determine the results of biological assays in a variety of applications including medical diagnostics, food safety, and forensic science. In some cases, it is necessary to perform several different assays on a single sample in a short period of time, wherein some of the different assays are mutually incompatible and therefore require separate processing. In other cases, many samples must be processed in a short period of time.

Deoxyribonucleic acid (DNA) sequencing is a prominent example of an application that benefits from parallel processing of many samples to sequence the DNA in a timely manner. Some of the more popular, commercially available DNA sequencing systems sequentially determine the order of nucleotide bases in a strand of DNA. Each base is determined through a biological assay followed by fluorescence imaging to determine the base type, i.e., adenine (A), guanine (G), cytosine (C), or thymine (T). The process to determine each base is time consuming and the overall sequencing process may have an occasional assay error leading to faulty sequencing. Therefore, the DNA strand is usually cut into a large number of shorter fragments that are processed in parallel.

DNA sequencing and many other DNA or ribonucleic acid (RNA) assays suffer from the amount of DNA or RNA material under investigation available being too low to produce a measurable result. In such situations, the DNA/RNA material may be amplified through polymerase chain reaction (PCR). PCR is a thermally mediated assay that produces many copies of a DNA or RNA molecule. The vast majority of PCR methods use thermal cycling of a sample, wherein each cycle duplicates the DNA or RNA material, eventually resulting in significant amplification of the original material. Isothermal amplification is an alternative to PCR, wherein the amplification takes place in an environment at a constant, elevated temperature.

SUMMARY

In an embodiment, a high-throughput fluorescence imaging system with sample heating capability includes an image sensor wafer with a plurality of image sensors for fluorescence imaging a plurality of samples disposed on the image sensor wafer. The high-throughput fluorescence imaging system further includes a plurality of fluidic channels for respectively containing the plurality of samples on the image sensor wafer, and a heating module, thermally coupled with the image sensor wafer, for heating the samples.

In an embodiment, a method for high-throughput assay processing includes (a) modulating temperature of a plurality of samples disposed in a respective plurality of fluidic channels on an image sensor wafer by heating the image sensor wafer, using a heating module thermally coupled with the image sensor wafer, to control reaction dynamics in the samples, and (b) capturing a plurality of fluorescence images of the samples, using a respective plurality of image sensors of the image sensor wafer, to detect one or more components of the plurality of samples.

In an embodiment, a method for manufacturing a high-throughput fluorescence imaging system with sample heating capability includes (a) bonding a fluidic wafer, including a plurality of fluidic channels, to an image sensor wafer including a plurality of image sensors, and (b) bonding a heating module, including a heater for generating heat, to the image sensor wafer to thermally couple the heater and the image sensor wafer.

DETAILED DESCRIPTION OF THE EMBODIMENTS

Figure 1:
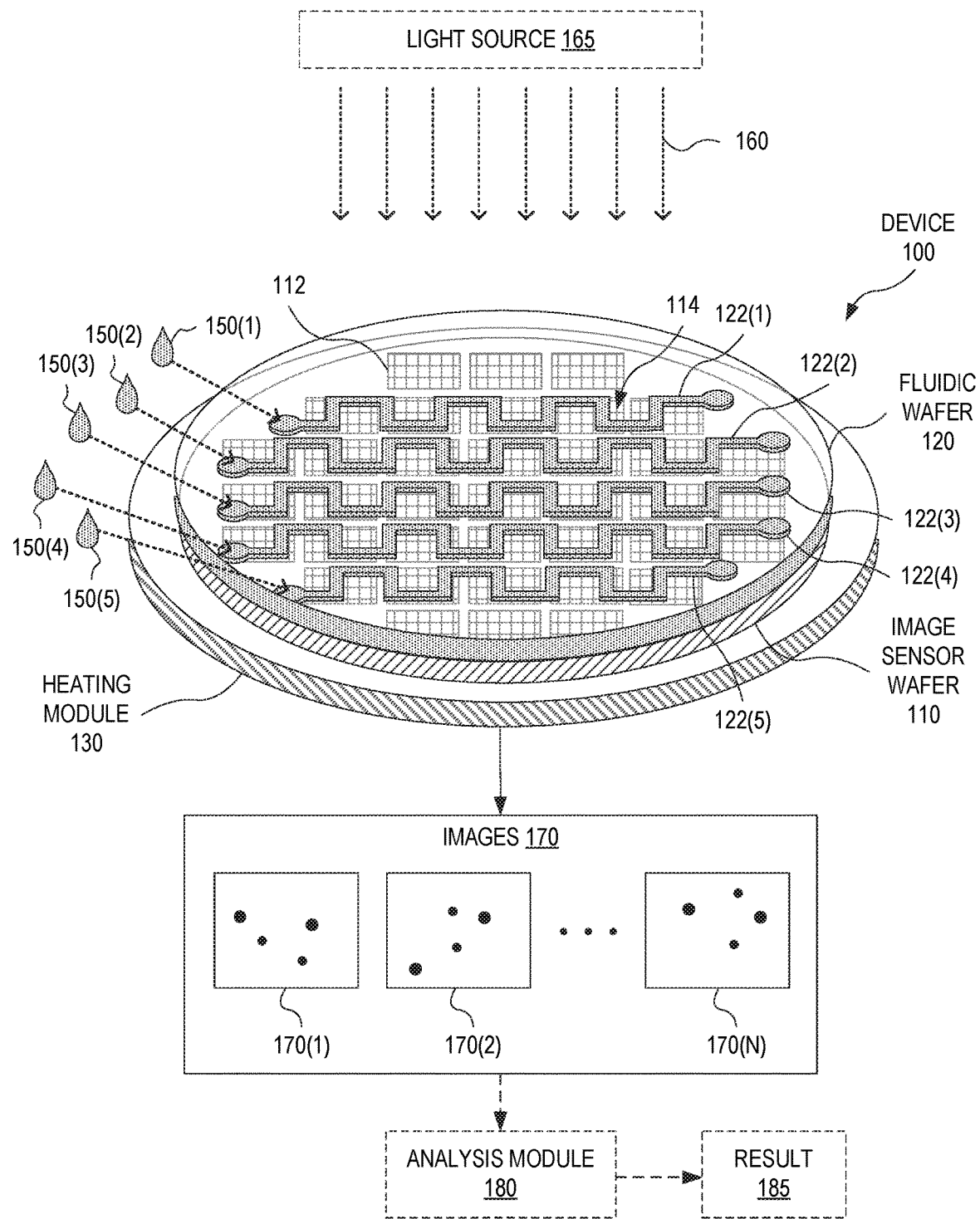
FIG. 1 illustrates a high-throughput fluorescence imaging device with sample heating capability, according to an embodiment.
Figure 2:
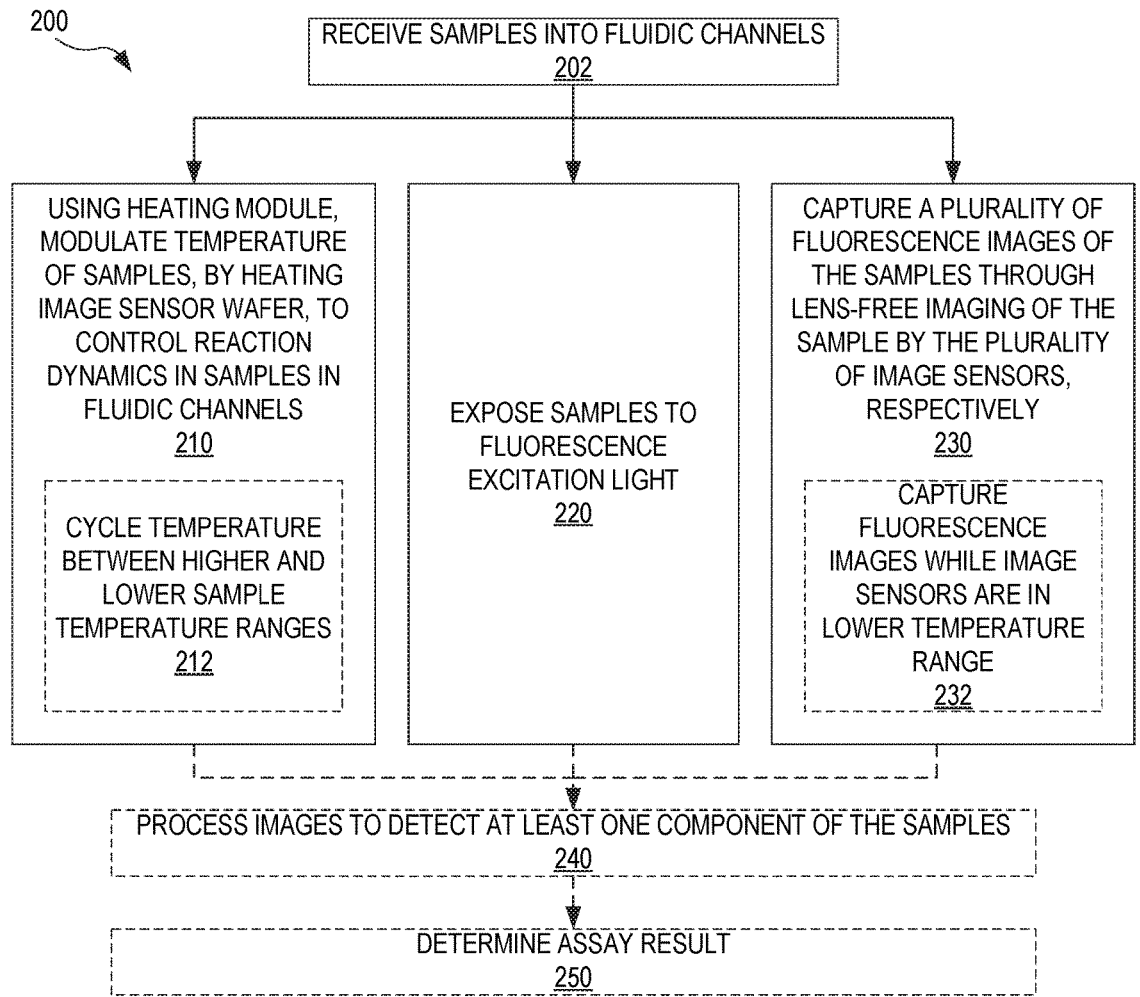
FIG. 2 illustrates a method for high-throughput, thermally mediated assay processing with fluorescence imaging readout, according to an embodiment.

FIG. 1 illustrates one exemplary high-throughput fluorescence imaging device 100 with sample heating capability. FIG. 2 illustrates one exemplary method 200 for high-throughput, thermally mediated assay processing with fluorescence imaging readout, using high-throughput fluorescence imaging device 100. FIGS. 1 and 2 are best viewed together.

High-throughput fluorescence imaging device 100 provides, in a relatively compact and cost-saving package, an integrated solution for processing multiple samples 150 in parallel. Processing of samples 150 by high-throughput fluorescence imaging device 100 includes modulating the temperature of samples 150 and imaging fluorescence of the samples 150 to determine a product of an assay that is, at least in part, thermally mediated. High-throughput fluorescence imaging device 100 may be manufactured using complementary metal-oxide-semiconductor (CMOS) manufacturing technology. CMOS manufacturing produces high-yield at low cost. Therefore, as compared to existing PCR and DNA sequencing devices, high-throughput fluorescence imaging device 100 may be produced at lower cost. In addition, CMOS manufacturing allows for precise manufacturing of very small features, such as micron or sub-micron sized features. Accordingly, high-throughput fluorescence imaging device 100 may operate on smaller volumes of samples 150 leading to reduced operation cost, as compared to existing PCR and DNA sequencing devices, while achieving high performance and high throughput.

Method 200 simultaneously processes a plurality of samples in parallel, for example to perform PCR or isothermal amplification of the samples and/or simultaneously sequence multiple DNA fragments. Fluorescence imaging device 100 includes an image sensor wafer 110 having a plurality of image sensors 112, a fluidic wafer 120 that cooperates with image sensor wafer 110 to form a plurality of fluidic channels 122, and a heating module 130. For clarity of illustration, not all image sensors 112 are labeled in FIG. 1. Fluidic wafer 120 is disposed on the light receiving surface 114 of image sensor wafer 110, such that fluidic channels 122 are in contact with light receiving surface 114 and in optical communication with a plurality of image sensors 112. In an embodiment, light-receiving surface 114 is planar or substantially planar. This eliminates the need for otherwise potentially costly imaging optics. Individual image sensors 112 cooperate to form a large surface and high-throughput fluorescence imaging device 100 is thus particularly well suited for processing and readout of surface based assays. Heating module 130 is thermally coupled with the surface of image sensor wafer 110 opposite light receiving surface 114. In certain embodiments, heating module 130 is in direct contact with image sensor wafer 110.

Image sensor 112 may be a charge-couple device (CCD) image sensor, a frontside-illuminated CMOS image sensor, or a backside-illuminated CMOS image sensor. Image sensor 112 may have megapixel resolution and may have surface area in the range from about 1 to about 50 square millimeters.

Although shown with five fluidic channels 122 in FIG. 1, high-throughput fluorescence imaging device 100 may include any number of fluidic channels 122 greater than one, without departing from the scope hereof. For example, high-throughput fluorescence imaging device 100 may include around tens, hundreds, thousands, or tens of thousands of fluidic channels 122. Likewise, image sensor wafer 110 may include any number of image sensors 112 greater than one, such as tens, hundreds, thousands, or tens of thousands of image sensors 112.

Fluidic channels 122 may have shapes different from those shown in FIG. 1, without departing from the scope hereof. For example, fluidic channels 122 may be straight, as opposed to serpentine shaped as shown in FIG. 1. Without departing from the scope hereof, fluidic channels 122 may cover a larger fraction of light-receiving surface 114 than illustrated in FIG. 1. For example, fluidic channels 122 may be closely spaced to reduce the area of portions of light-receiving surface 114 located between fluidic channels 122.

While shown in FIG. 1 as being circular, image sensor wafer 110, fluidic wafer 120, and heating module 130 may be of other shape, such as square or rectangular, without departing from the scope hereof.

In a step 202 of method 200, fluidic channels 122 receives samples 150.

In a step 210 of method 200, heating module 130 modulates the temperature of a plurality of samples 150, respectively disposed in fluidic channels 122, by heating image sensor wafer 110. Method 200 thus controls reaction dynamics in samples. The plurality of samples 150 may be mutually different, identical, or a combination thereof such that some samples 150 are different while other samples 150 are identical. Heating module 130 may heat image sensor wafer 110 continuously, temporarily, or repeatedly. In an embodiment, step 210 includes a step 212 of cycling the temperature of image sensor wafer 110 between higher and lower temperature ranges, thereby cycling the temperature of samples 150. Method 200 may utilize step 212 to perform PCR to amplify one or more components of samples 150.

In a step 220 of method 200, samples 150 are exposed to fluorescence excitation light 160. Optionally, high-throughput fluorescence imaging device 100 is coupled with, or includes, a light source 165 that provides fluorescence excitation light 160.

Light source 165 includes, for example, a light-emitting diode, a laser, and/or a white-light source. Light source 165 may further include a wavelength filter to form fluorescence excitation light 160 of desired wavelengths. Fluorescence excitation light 160 may include light in the infrared, near-infrared, visible, and/or ultraviolet wavelength ranges. Furthermore, light source 165 may be capable of selective emitting light of several different wavelengths to facilitate multi-colored and multiplexed fluorescence imaging.

In a step 230 of method 200, performed in parallel with step 220, each image sensor 112 captures a fluorescence image 170 of samples 150, through lens-free imaging of samples 150. In an embodiment, step 230 includes a step 232 of capturing fluorescence images 170 while image sensor wafer 110 is in a lower temperature range. Step 232 may provide fluorescence images 170 with less thermally induced noise than fluorescence images 170 captured while image sensor wafer 110 is in a higher temperature range. In the present disclosure, fluorescence images 170 may include a plurality of groups of fluorescence images 170 captured associated with a respective plurality of wavelengths of fluorescence excitation light 160 in step 220.

Step 210 is performed in parallel, in series, and/or alternatingly with steps 220 and 230.

Optionally, method 200 further includes a step 240 of processing fluorescence images 170 to detect at least one component of samples 150. Herein, a component of samples 150 refers to, for example, a molecule, a particle, a biological cell, a biological organism, a DNA strand of fragment, one or more proteins, and/or one or more nucleic acids. Step 240 may be followed by a step 250 that determines one or more assay results based upon detection of sample components in step 240. In one example, high-throughput fluorescence imaging device 100 is communicatively coupled with an analysis module 180 that performs step 240 and, optionally, step 250, to realize result 185. In another example, high-throughput fluorescence imaging device 100 may include analysis module 180.

It is to be understood that method 200 may include performing one or more assay steps, such as adding reagents not initially included in samples 150 and incubating such reagents with samples 150, without departing from the scope hereof. Such assay steps are performed, for example, according to methods known in the art.

Figure 3:
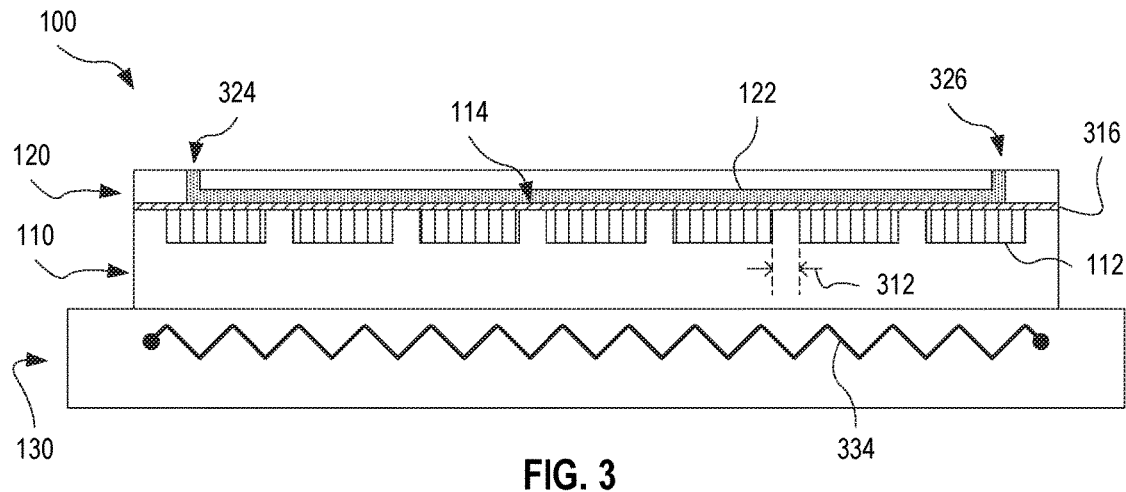
FIG. 3 is a cross-sectional side view showing the high-throughput fluorescence imaging device of FIG. 1 in more detail, according to an embodiment.

FIG. 3 is a cross-sectional side view showing high-throughput fluorescence imaging device 100 (FIG. 1) in more detail. The following discussion is concerned with features of high-throughput fluorescence imaging device 100 not shown in FIG. 1.

Image sensor wafer 110 includes a wavelength filter 316. Wavelength filter 316 suppresses fluorescence excitation light 160 such that image sensors 112 selectively detect fluorescence emission from samples 150. For clarity of illustration, not all image sensors 112 are labeled in FIG. 3. In one embodiment, wavelength filter 316 is further configured to provide color sensitivity for image sensors 112, to distinguish between fluorescence emission of different wavelengths. For example, each pixel of image sensors 112 may be associated with a portion of wavelength filter 316 that transmits light in a certain wavelength range, in a configuration similar to a Bayer pattern. In another embodiment, each image sensor 112 is a color image sensor with color sensitivity provided independently of wavelength filter 316. In yet another embodiment, high-throughput fluorescence imaging device 100 is configured to capture monochrome fluorescence images 170.

Image sensors 112 are separated by a distance 312. Certain embodiments of high-throughput fluorescence imaging device 100 minimize distance 312 to optimize the fraction of light receiving surface 114 associated with image sensors 112. In one embodiment, illustrated in FIG. 3, fluidic channel 122 is in optical communication with a plurality of image sensors 112. This may be beneficial in applications where the number of sample components of interest per unit area of light-receiving surface 114 is low. In another embodiment, fluidic channel 122 is in optical communication with a single image sensor 112 only. High-throughput fluorescence imaging device 100 may include a combination of (a) one or more fluidic channels 122 in optical communication with a plurality of image sensors 112 and (b) one or more fluidic channels 122 in optical communication with a single image sensor 112 only.

Each fluidic channel 122 includes fluidic ports 324 and 326. Fluidic ports 324 and/or 326 may receive sample 150.

Heating module 130 includes a heat source 334. Heat source 334 may be located on the surface of heating module 130 facing away from image sensor wafer 110, at the interface between heating module 130 and image sensor wafer 110, and/or in the interior of heating module 130. In one embodiment, heat source 334 is a resistive heater including one or more resistors, such as one or more thin-film platinum resistors. In another embodiment, heat source 334 is an induction heater including a metal and an electrical coil for inductively heating the metal. In yet another embodiment, heat source 334 is a metal that is inductively heated by an electrical coil located externally to high-throughput fluorescence imaging device 100.

Figure 4A:
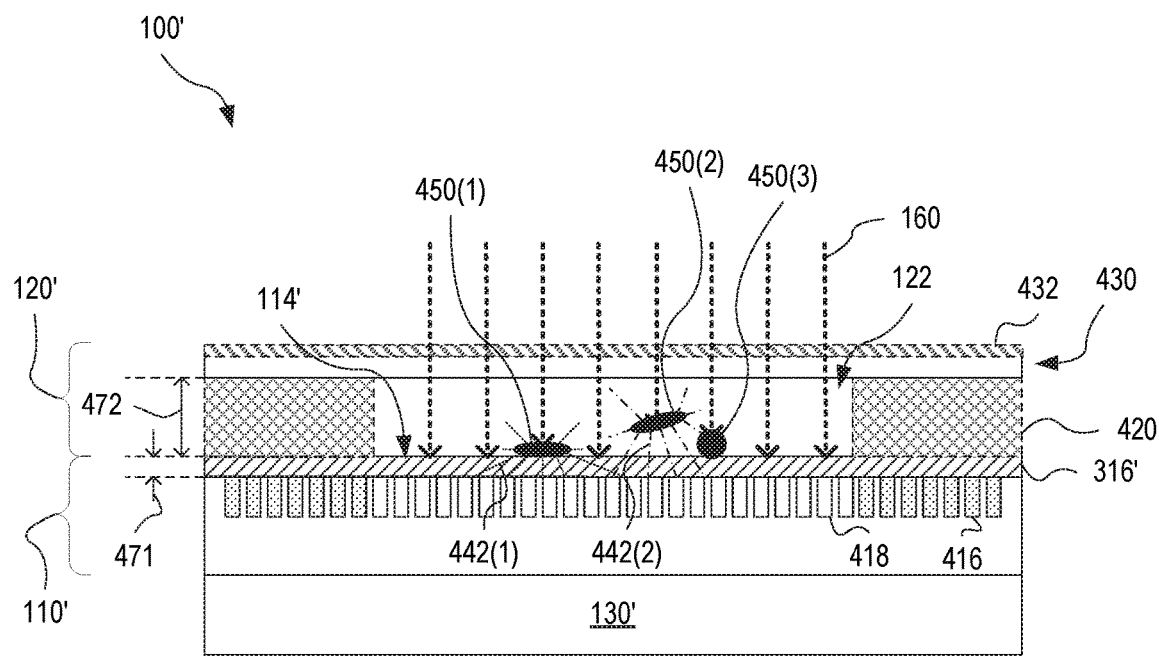
FIGS. 4A and 4B illustrate a portion of the high-throughput fluorescence imaging device of FIG. 1 together with lens-free fluorescence imaging of fluorescently labeled sample components, according to an embodiment.
Figure 4B:
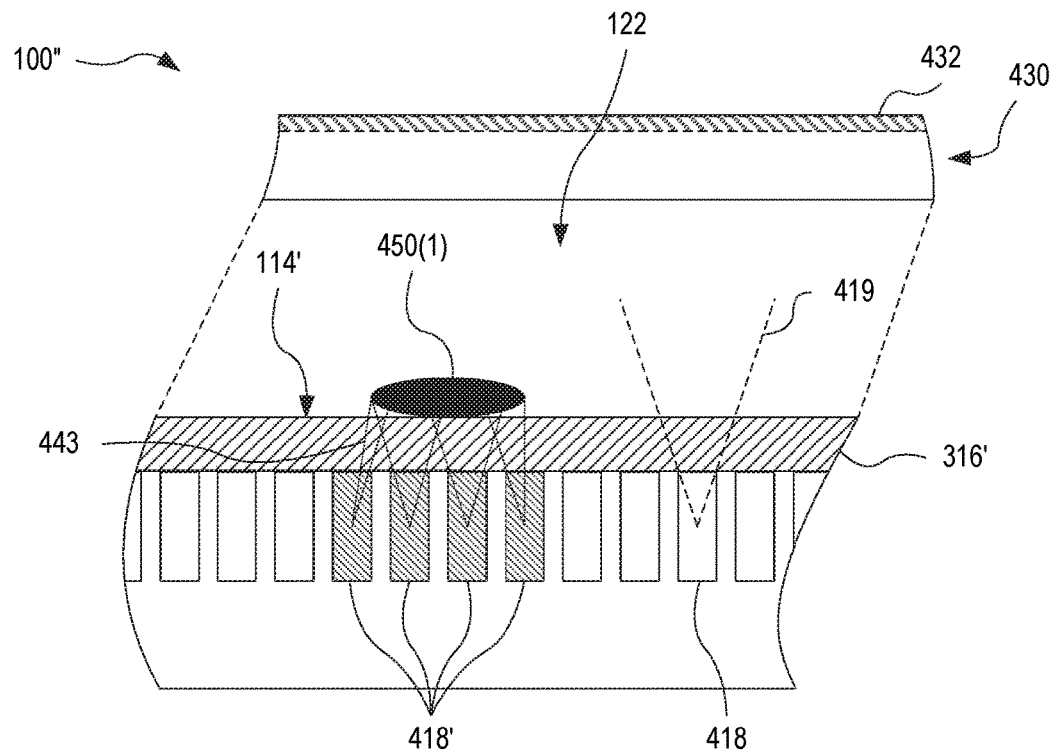

FIG. 4A illustrates one exemplary cross-sectional portion, device portion 100', of high-throughput fluorescence imaging device 100 (FIG. 1), together with lens-free fluorescence imaging of fluorescently labeled sample components 450(1) and 450(2) of sample 150. FIG. 4B shows a subsection 100" of device portion 100', which includes fluorescently labeled sample component 450(1). FIGS. 4A and 4B are best viewed together.

Device portion 100' includes an image sensor wafer portion 110' of image sensor wafer 110, a fluidic wafer portion 120' of fluidic wafer 120, and a heating module portion 130' of heating module 130. Image sensor wafer portion 110' includes a light receiving surface 114', which is a portion of light receiving surface 114, a wavelength filter 316', which is a portion of wavelength filter 316 (FIG. 3), and a plurality of photosensitive pixels 418 in optical communication with fluidic channel 122 of fluidic wafer portion 120'. Photosensitive pixels 418 indicated in FIGS. 4A and 4B may belong to a single image sensor 112 or a plurality of image sensors 112. For clarity of illustration, not all pixels 418 are labeled in FIGS. 4A and 4B.

Fluidic wafer portion 120' includes a chamber composed of a cover 430 and walls 420. Cover 430 and walls 420 are configured to create a recess in fluidic wafer portion 120'. This recess cooperates with light receiving surface 114' of image sensor wafer portion 110' to form fluidic channel 122. In one embodiment, walls 420 and cover 430 are integrally formed. For example, the recess that cooperates with light receiving surface 114' to form fluidic channel 122 may be produced by removing material from a planar substrate or by molding a material to the shape of cover 430 and walls 420. In another embodiment, walls 420 and cover 430 are separate elements combined to create the recess that cooperate with light receiving surface 114' to form fluidic channel 122. In this embodiment, cover 430 may be at least partially optically transmissive, while walls 420 may be opaque or mostly opaque to fluorescence excitation light 160.

In an embodiment, cover 430, and optionally walls 420, blocks or partially blocks light of certain wavelengths to reduce contribution of fluorescence excitation light 160 to signal in fluorescence images 170. In one example, cover 430 includes a wavelength filter coating 432 that filters fluorescence excitation light to block or reduce light of wavelengths transmitted by wavelength filter 316'. In another example, cover 430, and optionally walls 420, are formed from a material that blocks or partially blocks light of certain wavelengths, such as those transmitted by wavelength filter 316'.

Optionally, image sensor wafer portion 110' includes photosensitive pixels 416 located underneath walls 420. For clarity of illustration, not all pixels 416 are labeled in FIG. 4A. In one example of use, pixels 416 are dark pixels used to measure electronic noise associated with pixels 416 and 418. Such electronic noise measured by pixels 416 may be subtracted from signals recorded by pixels 418 to produce a noise-subtracted fluorescence image 170. This is particularly useful if pixels 418 are active in fluorescence image capture by high-throughput fluorescence imaging device 100 while image sensor wafer 110, or portions thereof, is at an elevated temperature leading to increased thermally-induced electronic noise.

Pixels 418 capture at least a portion of one or more fluorescence images 170 of sample 150 in fluidic channel 122. As discussed in connection with FIG. 2, fluorescence image(s) 170 is formed by exposing fluidic channel 122 to fluorescence excitation light 160. In the exemplary scenario illustrated in FIG. 4A, fluorescence excitation light 160 excites fluorophores on, and/or in, sample components 450(1) and 450(2). Sample components 450(1) and 450(2) respond to fluorescence excitation light 160 by emitting fluorescence emission 442(1) and 442(2), respectively. Sample component 450(3) is not fluorescently labeled. Therefore, sample component 450(3) does not generate fluorescence emission when illuminated with fluorescence excitation light 160. At least portions of fluorescence emission 442(1) and 442(2) are transmitted by wavelength filter 316' to pixels 418. Hence, pixels 418 detect at least portions of fluorescence emission 442(1) and 442(2), whereby pixels 418 detect fluorescently labeled sample components 450(1) and 450(2). Since sample component 450(3) is not fluorescently labeled, sample component 450(3) is not detected by pixels 418. Accordingly, pixels 418 generate at least a portion of one or more fluorescence images 170 indicating fluorescently labeled sample components 450(1) and 450(2).

Subsection 100'' includes fluorescently labeled sample component 450(1). Each pixel 418 has an acceptance angle 419. For clarity of illustration, acceptance angle 419 is indicated only for one pixel 418. In an embodiment, acceptance angle 419 and the distance 471 from light receiving surface 114' to pixels 418 are such that only pixels 418 located close to fluorescently labeled sample component 450(1) are capable of detecting fluorescence emission 442(1) originating from fluorescently labeled sample component 450(1). These pixels are labeled 418' in FIG. 4B. For pixels 418', lines 443 outline the portion of acceptance angle 419 that includes a line of sight to fluorescently labeled sample component 450(1). Other pixels 418 do not include a line of sight to fluorescently labeled sample component 450(1) that is within acceptance angle 419.

In an embodiment, acceptance angle 419 and distance 471 are such that only pixels 418 at locations less than one pixel 418 away, in a direction parallel to light receiving surface 114', are capable of detecting fluorescence emission from a fluorescently labeled sample component located on light receiving surface 114'. In this embodiment, pixels 418 together generate minimally blurred fluorescence image(s) 170, or a portion thereof, of fluorescently labeled sample components on light receiving surface 114'. In another embodiment, acceptance angle 419 and distance 471 cooperate to result in the rate of occurrence of overlapping fluorescence events, in a fluorescence image 170 of a sample 150 containing fluorescently labeled sample components of interest at a typical concentration, being below a desired threshold. In yet another embodiment, acceptance angle 419 is sufficiently small that fluorescence image(s) 170 of a sample 150 containing uniformly spaced fluorescently labeled sample components of interest at a typical concentration is free of overlapping fluorescence events.

For imaging of samples 150, in which the sample components of interest do not necessarily settle to light receiving surface 114', blur is minimized when the height 472 of fluidic channel 122 is small. Therefore, in certain embodiments of high-throughput fluorescence imaging device 100, height 472 is the minimal height that allows for depositing sample 150 in fluidic channel 122.

In one embodiment, height 472 is less than 10 micron or less than 1 micron. Such low values of height 472 minimize the required volume of samples 150 and any associated assay reagents. In another embodiment, height 472 is greater than 10 micron, for example hundreds of microns or millimeter-sized.

In an embodiment, the size of pixels 418 is significantly smaller than the size of fluorescently labeled sample components of interest in fluidic channel 122, wherein the size of a pixel 418 is defined as the largest dimension of pixel 418 in a plane parallel to light receiving surface 114'. This allows for accurate size and shape determination of fluorescently labeled sample components of interest, and may further allow for identification of a fluorescently labeled sample components of interest based upon fluorescence detection and the size of the fluorescence event in fluorescence image 170. For example, a fluorescently labeled sample component of interest may be found as a subset of detected fluorescence events that further meet specified size and/or shape criteria.

Figure 5A:
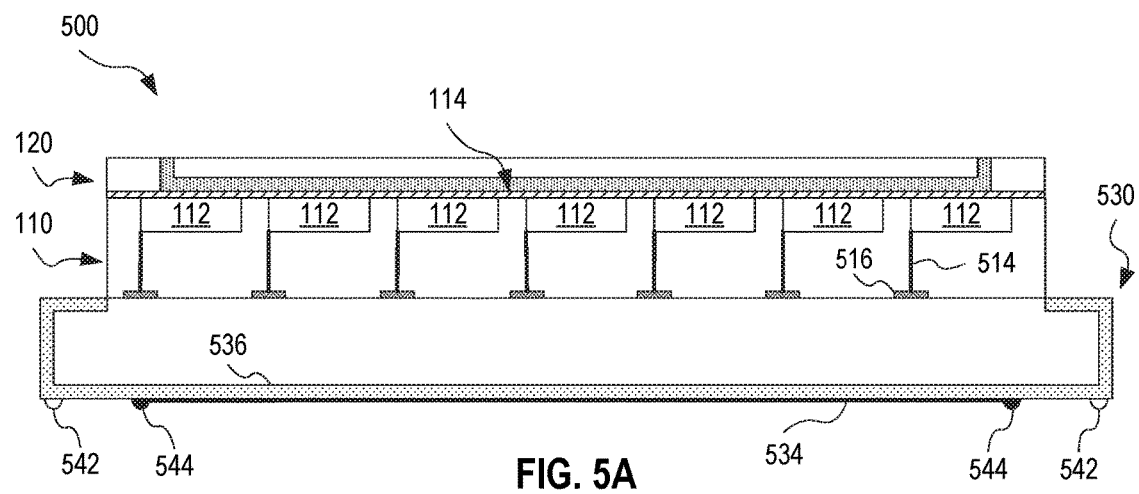
FIGS. 5A and 5B illustrate a high-throughput fluorescence imaging device with the heat source located on a surface of the heating module that faces away from the image sensor wafer, according to an embodiment.
Figure 5B:
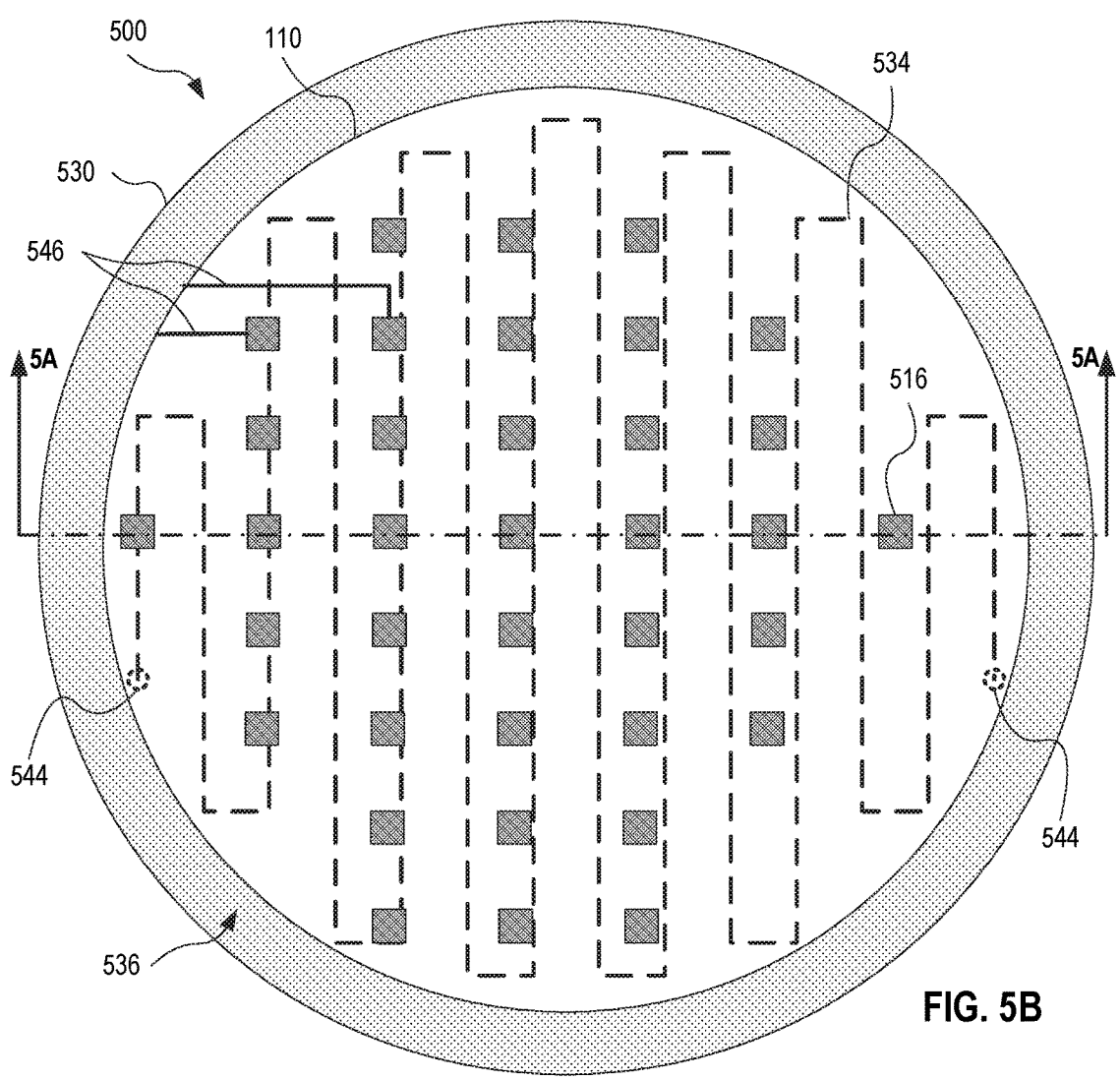

FIGS. 5A and 5B illustrate one exemplary high-throughput fluorescence imaging device 500 with the heat source located on a surface of the heating module that faces away from the image sensor wafer. High-throughput fluorescence imaging device 500 is an embodiment of high-throughput fluorescence imaging device 100 (FIG. 1) and includes image sensor wafer 110, fluidic wafer 120, and a heating module 530. FIG. 5A is a cross-sectional side view of high-throughput fluorescence imaging device 500 taken along line 5A-5A in FIG. 5B. FIG. 5B is a cross-sectional top view of high-throughput fluorescence imaging device 500 taken along the interface between image sensor wafer 110 and heating module 530. FIGS. 5A and 5B are best viewed together.

Heating module 530 is an embodiment of heating module 130. Heating module 530 includes a resistive heat source 534, an embodiment of heat source 334 (FIG. 3), located on a surface of heating module 530 facing away from image sensor wafer 110. Resistive heat source 534 includes one or more resistors, such as one or more thin-film platinum resistors. Resistive heat source 534 includes at least two electrical contacts 544 for passing current through resistive heat source 534 to generate heat. Although resistive heat source 534 is located outside the cross-sectional view of FIG. 5B, the projected position of heat source 534 is nevertheless indicated as a dashed line in FIG. 5B. Resistive heat source 534 may be arranged in a serpentine pattern, as illustrated in FIG. 5B, or in a different pattern such as a spiral pattern or a single loop, without departing from the scope hereof.

Image sensor wafer 110 includes electrical connections 514 from image sensors 112 to electrical connection pads 516 located at the interface between image sensor wafer 110 and heating module 130. For clarity of illustration, FIGS. 5A and 5B show only one electrical connection 514 and only one electrical connection pad 516 for each image sensor 112. However, each of one or more of image sensors 112 may be associated with several electrical connections 514 and or several electrical connection pads 516, without departing from the scope hereof. Also for clarity of illustration, only one electrical connection 514 is labeled in FIG. 5A, and only one electrical connection pad 516 is labeled in each of FIGS. 5A and 5B. High-throughput fluorescence imaging device 500 further includes electrical connections 546 that connect electrical connection pads 516 to a region 536 of heating module 530. For clarity of illustration, FIG. 5B shows only two electrical connections 546. Region 536 is the surface portion of heating module 530 that is accessible from outside high-throughput fluorescence imaging device 500. Region 536 includes image readout contacts 542 forming an interface for reading out fluorescence images 170 captured by image sensors 112. For clarity of illustration, only two image readout contacts 542 are shown in each of FIGS. 5A and 5B. However, high-throughput fluorescence imaging device 500 may include more than two image readout contacts 542, or even just one image readout contact 542, without departing from the scope hereof. Furthermore, image readout contacts 542 may be located anywhere in area 536 as long as image readout contacts 542 do not interfere with resistive heat source 534.

Since resistive heat source 534 is located on a surface of heating module 130 facing away from image sensor wafer 110, electrical connection pads 516 and electrical connections 546 do not interfere with resistive heat source 534. Additionally, image readout contacts 542 may be located such that electronic circuitry associated with communication between image sensors 112 and image readout contacts 542 (and/or other electronic circuitry associated with processing of electrical signals from or to image sensors 112) does not interfere with resistive heat source 534.

Figure 6A:
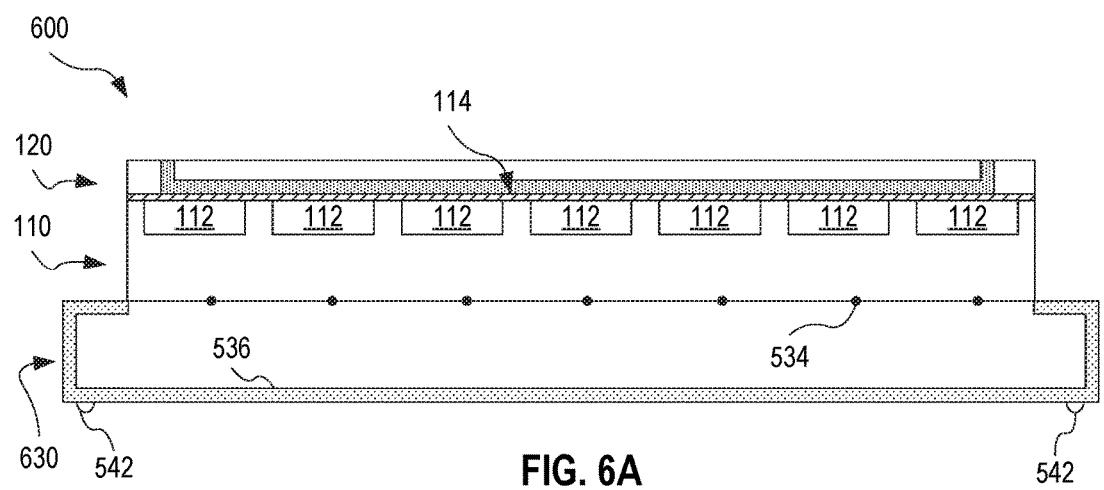
FIGS. 6A and 6B illustrate a high-throughput fluorescence imaging device with the heat source located at the interface between the heating module and the image sensor wafer, according to an embodiment.
Figure 6B:
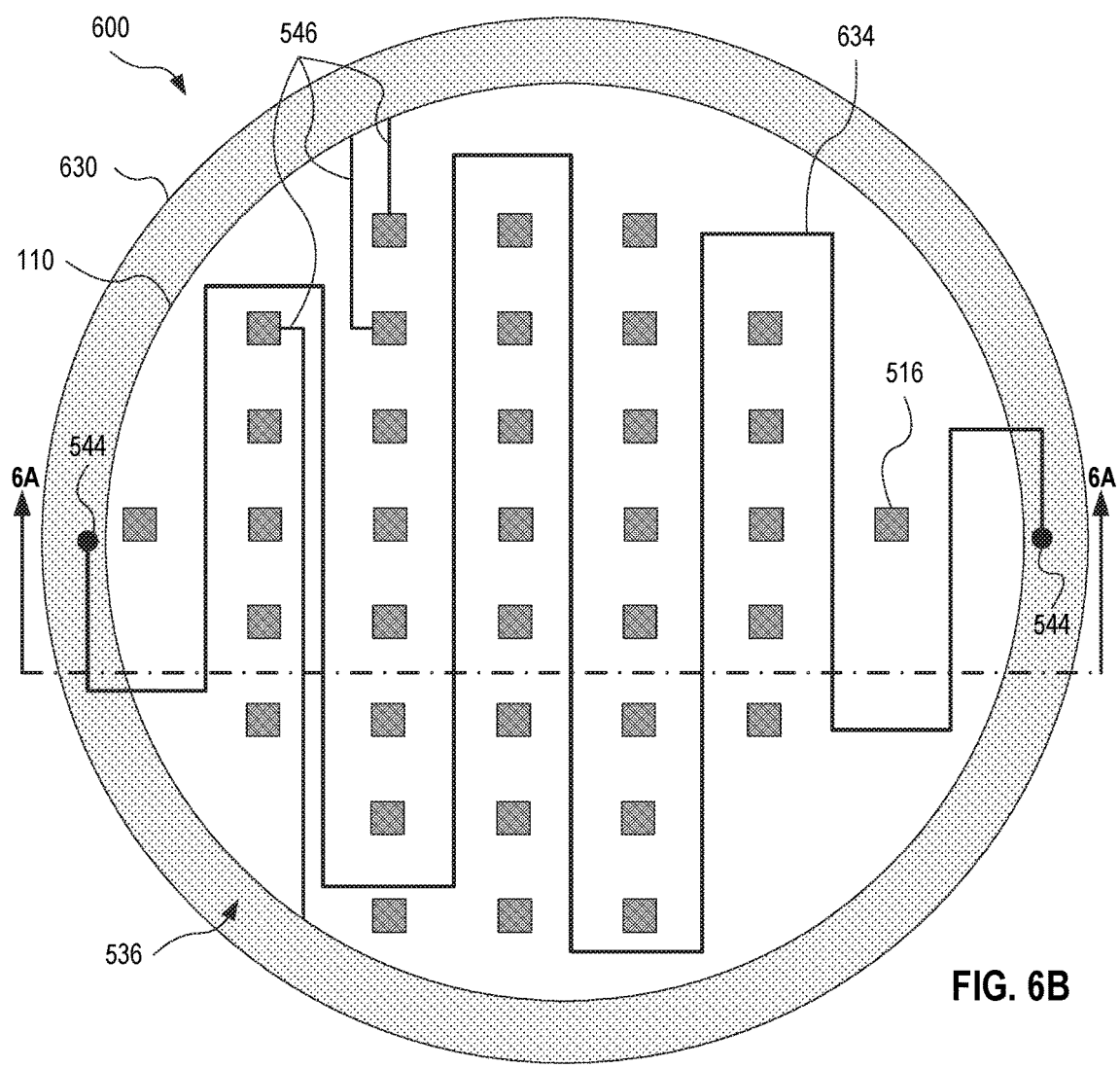

FIGS. 6A and 6B illustrate one exemplary high-throughput fluorescence imaging device 600 with the heat source located at the interface between the heating module and the image sensor wafer. High-throughput fluorescence imaging device 600 is an embodiment of high-throughput fluorescence imaging device 100 (FIG. 1) and is similar to high-throughput fluorescence imaging device 500 (FIG. 5). As compared to high-fluorescence imaging device 500, high-fluorescence imaging system 500 includes a heating module 630 instead of heating module 530. FIG. 6B is analogous to the cross-sectional top view of FIG. 5B. FIG. 6A is a cross-sectional side view of high-throughput fluorescence imaging device 600 taken along line 6A-6A in FIG. 6B. FIGS. 6A and 6B are best viewed together. The following discussion is concerned with features of heating module 630 that differ from heating module 530.

Heating module 630 includes a resistive heat source 634 at the interface between image sensor wafer 110 and heating module 630. Resistive heat source 634 is an embodiment of heat source 334 (FIG. 3), similar to resistive heat source 534 (FIG. 5), that weaves through electrical connections 546 without interfering with electrical connections 546 or electrical connection pads 516. Heating module 630 may implement electrical contacts 544 in a portion of region 536 facing toward image sensor wafer 110 without contacting image sensor wafer 110, as illustrated in FIG. 6B, or in another location within region 536.

Figure 7:
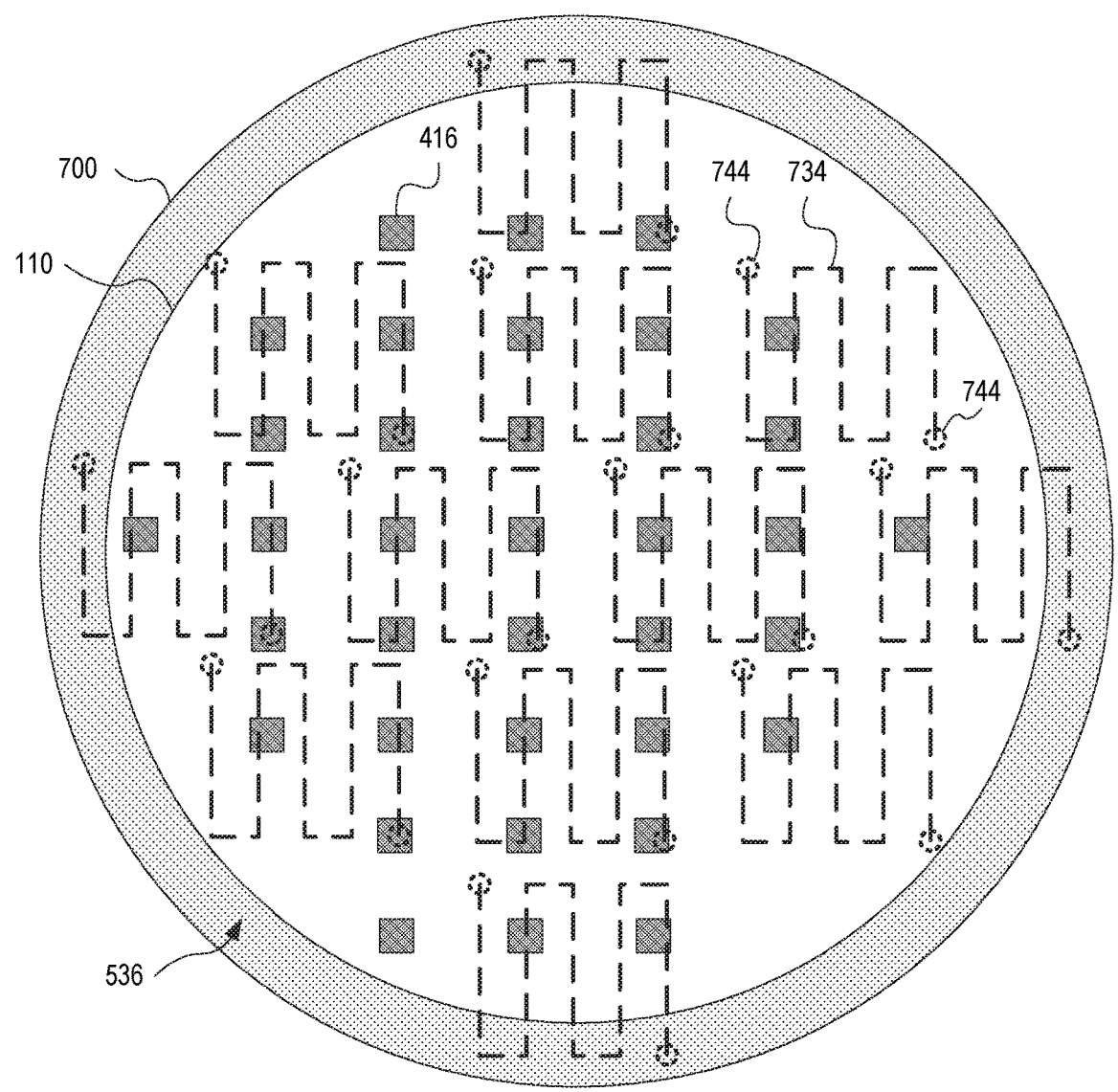
FIG. 7 illustrates a heating module capable of separately heating different portions of an image sensor wafer, according to an embodiment.

FIG. 7 illustrates one exemplary heating module 700 capable of separately heating different portions of image sensor wafer 110 (FIG. 1), thus enabling position-sensitive temperature control of image sensor wafer 110. Heating module 700 is similar to heating module 530 of high-throughput fluorescence imaging device 500 (FIG. 5). FIG. 7 shows heating module 700 as being implemented in high-throughput fluorescence imaging device 500 instead of heating module 530. FIG. 7 is a cross-sectional top view analogous to that of FIG. 5B.

Heating module 700 is similar to heating module 530 except that heating module 700 includes a plurality of resistive heat sources 734. Resistive heat sources 734 are located on the surface of heating module 700 facing away from image sensor wafer 110. FIG. 7 shows the projection of resistive heat sources 734 onto the cross-sectional top view of FIG. 7 as dashed lines. Resistive heat source 734 is similar to resistive heat source 534 and includes electrical contacts 744 that are similar to electrical contacts 544. For clarity of illustration, only one resistive heat source 734 is labeled in FIG. 7.

Although not illustrated in FIG. 7, resistive heat sources 734 may be located at the interface between heating module 700 and image sensor wafer 110, in which case additional electrical connections are incorporated into heating module 700 to connect electrical contacts 734 to region 536.

Figure 8:
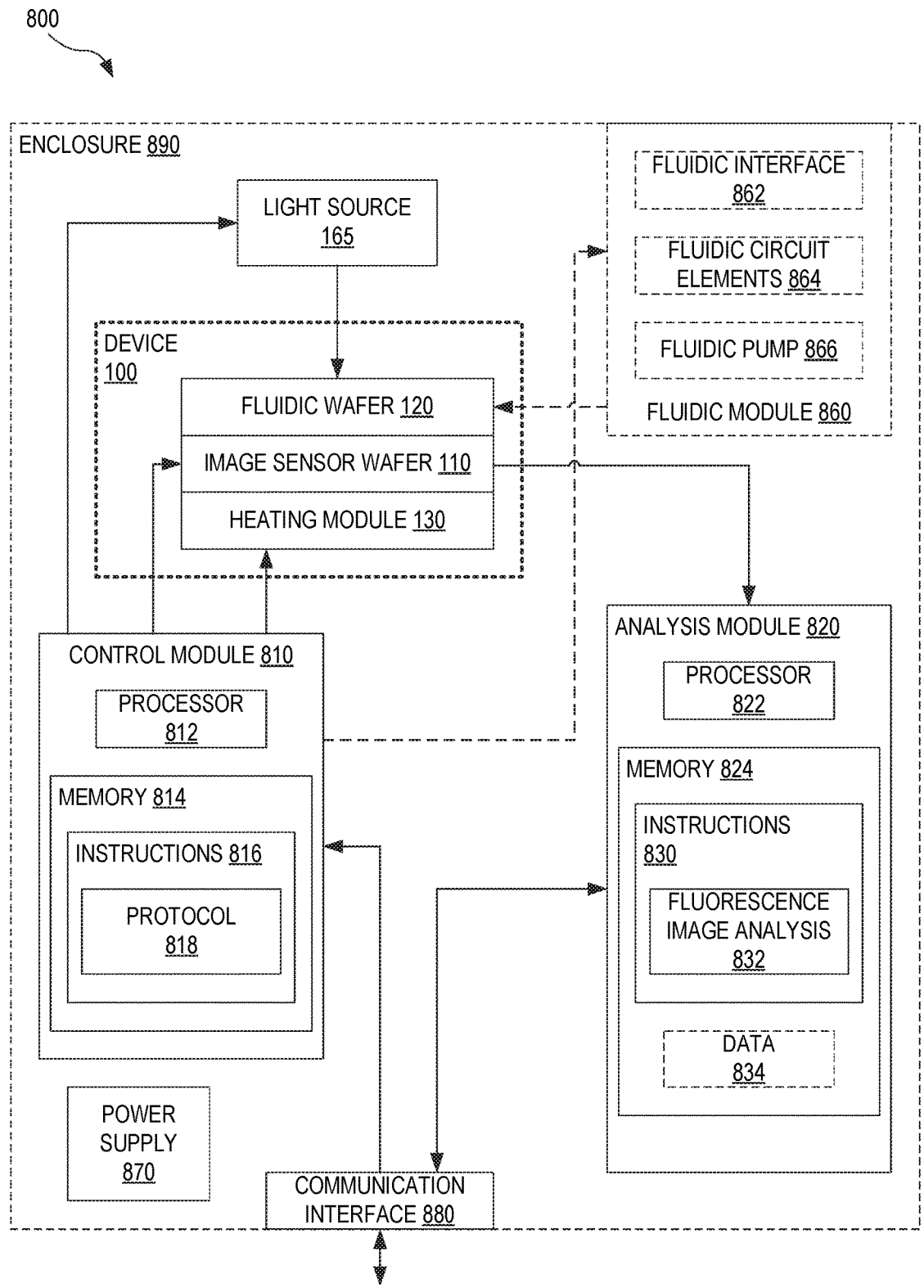
FIG. 8 illustrates a high-throughput fluorescence imaging system that receives the high-throughput fluorescence imaging device of FIG. 1 to perform the method of FIG. 2, according to an embodiment.

FIG. 8 illustrates one exemplary high-throughput fluorescence imaging system 800 that receives high-throughput fluorescence imaging device 100 (FIG. 1) and controls functionality of high-throughput fluorescence imaging device 100 to process multiple samples 150 in parallel according to method 200 (FIG. 2). High-throughput fluorescence imaging system 800 includes light source 165, a control module 810 communicatively coupled with high-throughput fluorescence imaging device 100 and light source 165, and an analysis module 820 communicatively with high-throughput fluorescence imaging device 100. Although not illustrated in FIG. 8, control module 810 and/or analysis module 820 may be communicatively coupled with image sensor wafer 110 via heating module 130, for example as discussed in reference to FIGS. 5A and 5B.

High-throughput fluorescence imaging system 800 further includes a power supply 870 that supplies power at least to control module 810 and analysis module 820. Additionally, high-throughput fluorescence imaging system 800 includes a communication interface 880 that facilitates communication between (a) a user and/or an external computer system and (b) control module 810 and analysis module 820.

Control module 810 includes a processor 812 and a memory 814 with machine-readable instructions 816 stored to non-transitory media within memory 814. High-throughput fluorescence imaging system 800 implements steps 202, 210, 220, and 230 of method 200 as protocol 818 within machine-readable instructions 816.

In an embodiment, high-throughput fluorescence imaging system 800 includes a fluidic module 860 that controls at least portions of fluid handling associated with processing of samples 150. In this embodiment, machine-readable instructions 816 may further include instructions that, upon execution by processor 812, controls fluidic module 860. Fluidic module 860 includes a fluidic interface 862 that receives samples 150 and, in some cases, assay reagents used to process samples 150. Fluidic module 860 also includes fluidic circuit elements 864 such as fluidic channels and valves. Fluidic module 860 may further include a fluidic pump 866 that pumps samples 150, and optionally assay reagents, to and/or from fluidic channels 122 of fluidic wafer 120.

Analysis module 820 includes a processor 822, a memory 824 with machine-readable instructions 830 stored to a non-transitory portion of memory 824, and an optional data storage 834 used for example to store fluorescence images 170. High-throughput fluorescence imaging system 800 implements step 240 and, optionally, step 250 as fluorescence image analysis instructions 832 within machine-readable instructions 830.

Communication interface 880 may receive instructions from a user and/or a system external to high-throughput fluorescence imaging system 800, and communicate such instructions to one or both of control module 810 and analysis module 820. For example, communication interface 880 may communicate protocol 818 to control module 810. Analysis module 820 communicates fluorescence images 170 and/or result 185 derived from fluorescence images 170 via communication interface 880 to a user and/or a system external to high-throughput fluorescence imaging system 800. In addition, communication interface 880 may receive fluorescence image analysis instructions 830 from communication interface 880.

High-throughput fluorescence imaging system 800 may include an enclosure 890 with one or more openings at least capable of accepting high-throughput fluorescence imaging device 100 and, optionally, samples 150.

Figure 9:
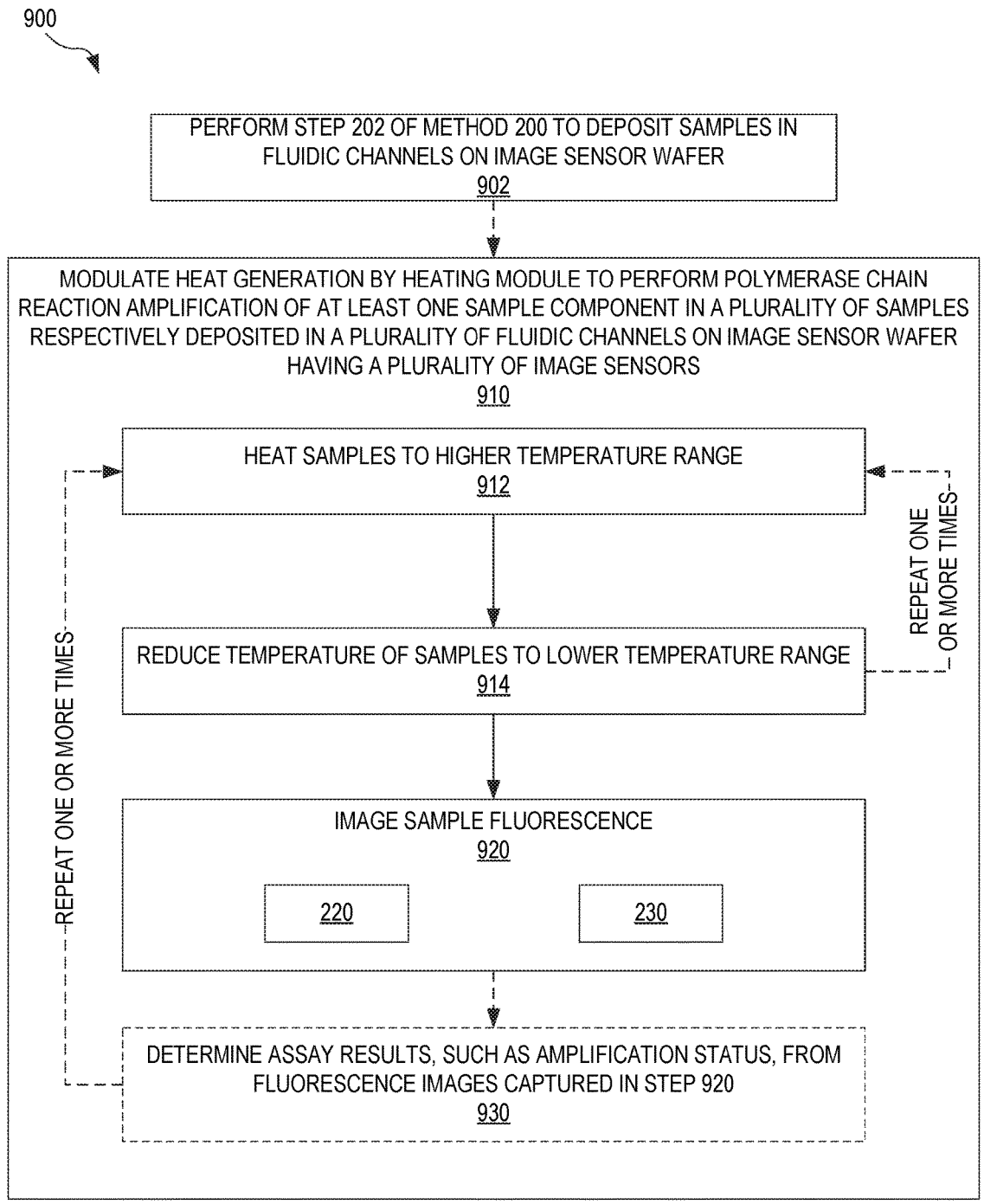
FIG. 9 illustrates a method for high-throughput, PCR amplification and fluorescence imaging readout of a plurality of samples, according to an embodiment.

FIG. 9 illustrates one exemplary method 900 for high-throughput, PCR amplification and fluorescence imaging readout of samples 150, using high-throughput fluorescence imaging device 100 (FIG. 1). Method 900 is an embodiment of method 200 (FIG. 2). High-throughput fluorescence imaging system 800 (FIG. 8) may implement method 900 as machine-readable instructions composed of protocol 818 and fluorescence image analysis instructions 832.

In a step 902, method 900 performs step 202 of method 200 to deposit samples 150 in fluidic channels 122. In one example of step 902, fluidic module 860 receives samples 150 via fluidic interface 862 and deposits samples 150 in fluidic channels 122.

In a step 910, heat generation by heating module 130 is modulated to perform PCR amplification of at least one of sample component in samples 150. Step 910 includes steps 912, 914, 920, and, optionally, 930.

In step 912, heating module 130 heats samples 150 to a higher temperature range than ambient temperature, such as a temperature in the range between 50 and 100 degrees Celsius. In one example of step 912, processor 812 of control module 810 executes at least a portion of protocol 818 to turn on a desired level of heat generation by heating module 130. Optionally, high-throughput fluorescence imaging device 100 is implemented with a plurality of heat sources, as discussed in reference to FIG. 7, which are controlled individually by control module 810 to selectively heat certain portions of high-throughput fluorescence imaging device 100.

In a step 914, heat generation by heating module 130 is turned off or reduced to reduce the temperature of samples 150 to a lower temperature range such as ambient temperature. In one example of step 914, processor 812 of control module 810 executes at least a portion of protocol 818 to turn off or reduce heat generation by heating module 130.

In an embodiment, method 900 returns to step 912 after completion of step 914. Method 900 may repeat sequential steps 912 and 914 several times before proceeding the subsequent step 920.

In step 920, method 900 captures fluorescence images 170 of samples 150, by performing parallel steps 220 and 230 of method 200. In one example of step 920, control module 810 executes at least a portion of protocol 818 to turn on light source 165 and trigger image capture by image sensors 112.

In an optional step 930, method 900 determines assay results 185 based upon fluorescence images 170 captured in step 920. In one embodiment, assay result 185 is amplification status of certain components of samples 150 such as a plurality of DNA strands. In another embodiment, assay result 185 is the presence, and optionally amount, of one or more components of interest in samples 150. In one example of step 930, processor 822 executes fluorescence image analysis instructions 832 to (a) identify, in fluorescence images 170, fluorescence events associated with at least one sample component of interest in samples 150 and (b) analyze such fluorescence events to determine assay result 185.

In one embodiment, method 900 repeats sequential steps 912, 914, 920, and 930 several times to perform several PCR cycles (steps 912 and 914) and, for each of the PCR cycles, monitor amplification status of at least one component of samples 150 or monitor presence of at least one component of interest in samples 150 (steps 920 and 930). Method 900 may terminate step 910 when achieving a desired assay result 185 in step 930. Although not illustrated in FIG. 9, method 900 may repeat steps 912 and 914 to perform several PCR cycles, and further perform steps 920 and 930 for at least one of those cycles, without departing from the scope hereof.

Figure 10:
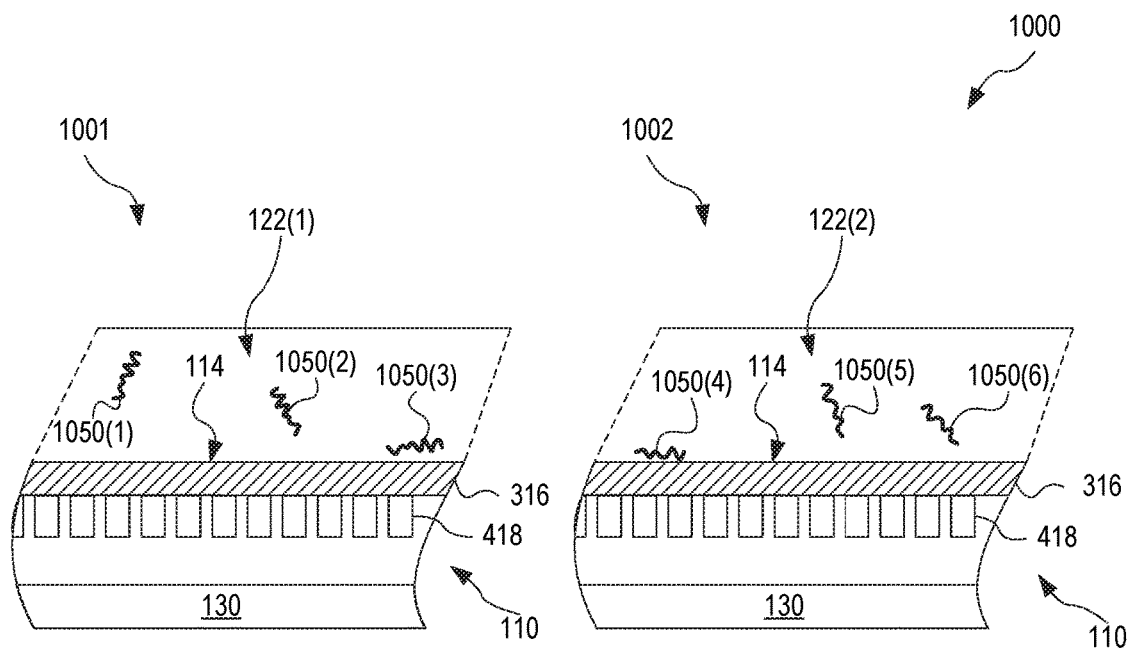
FIG. 10 illustrates a scenario for processing a plurality of samples, according to an embodiment.

FIG. 10 illustrates one exemplary scenario 1000 for processing of samples 150 (FIG. 1) that may apply to either of method 200 (FIG. 2) and method 900 (FIG. 9). In scenario 1000, two portions 1001 and 1002 of high-throughput fluorescence imaging device 100 (FIG. 1) are associated with two different fluidic channels 122(1) and 122(2). Fluidic channel 122(1) includes components 1050(1), 1050(2), and 1050(3) of one sample 150, while fluidic channel 122(2) includes components 1050(4), 1050(5), and 1050(6) of another sample 150. Components 1050 are not attached to light receiving surface 114. Components 1050 are, for example, a DNA strand, RNA, or other nucleic acid based molecule.

In one example, components 1050 represent the status of samples 150 after performing step 202 of method 200 or step 902 of method 900.

In another example, components 1050 represent the status of samples 150 during at least portions of steps 210, 220, and 230 of method 200 or during at least portions of step 910 of method 900.

Components 1050 may indicate sample components of interest to be amplified by PCR using method 900. For example, components 1050(1), 1050(2), and 1050(3) are identical, and components 1050(4), 1050(5), and 1050(6) are identical, while components 1050(1), 1050(2), and 1050 (3) are different from components 1050(4), 1050(5), and 1050(6), such that fluidic channels 122(1) and 122(2) are respectively associated with PCR amplification of two different types of sample component 1050.

Figure 11:
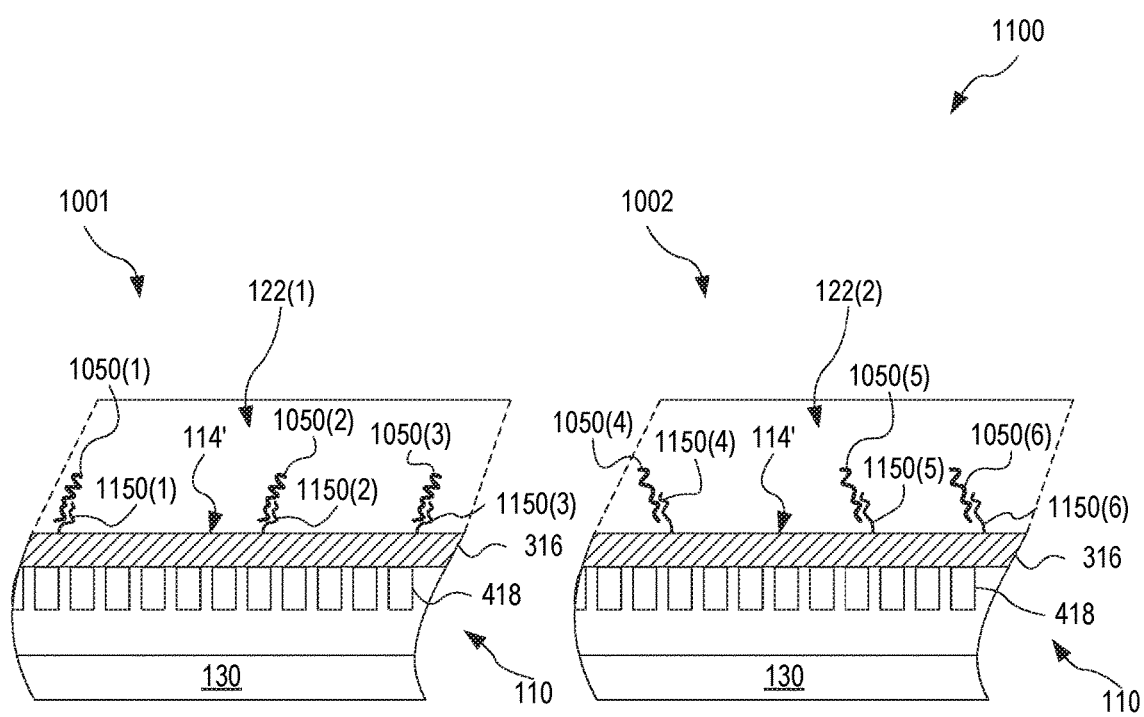
FIG. 11 illustrates another scenario for processing a plurality of samples, according to an embodiment.

FIG. 11 illustrates another exemplary scenario 1100 for processing samples 150 (FIG. 1) that may apply to either of method 200 (FIG. 2) and method 900 (FIG. 9). In scenario 1100, components 1050 are attached to light receiving surface 114 via corresponding capture molecules 1150. High-throughput fluorescence imaging device 100 may include capture molecules 1150 to enable surface capture of components 1050, or such capture molecules may be provided in step 202 of method 200, step 902 of method 900, or another assay step not illustrated in FIGS. 2 and 9.

Figure 12:
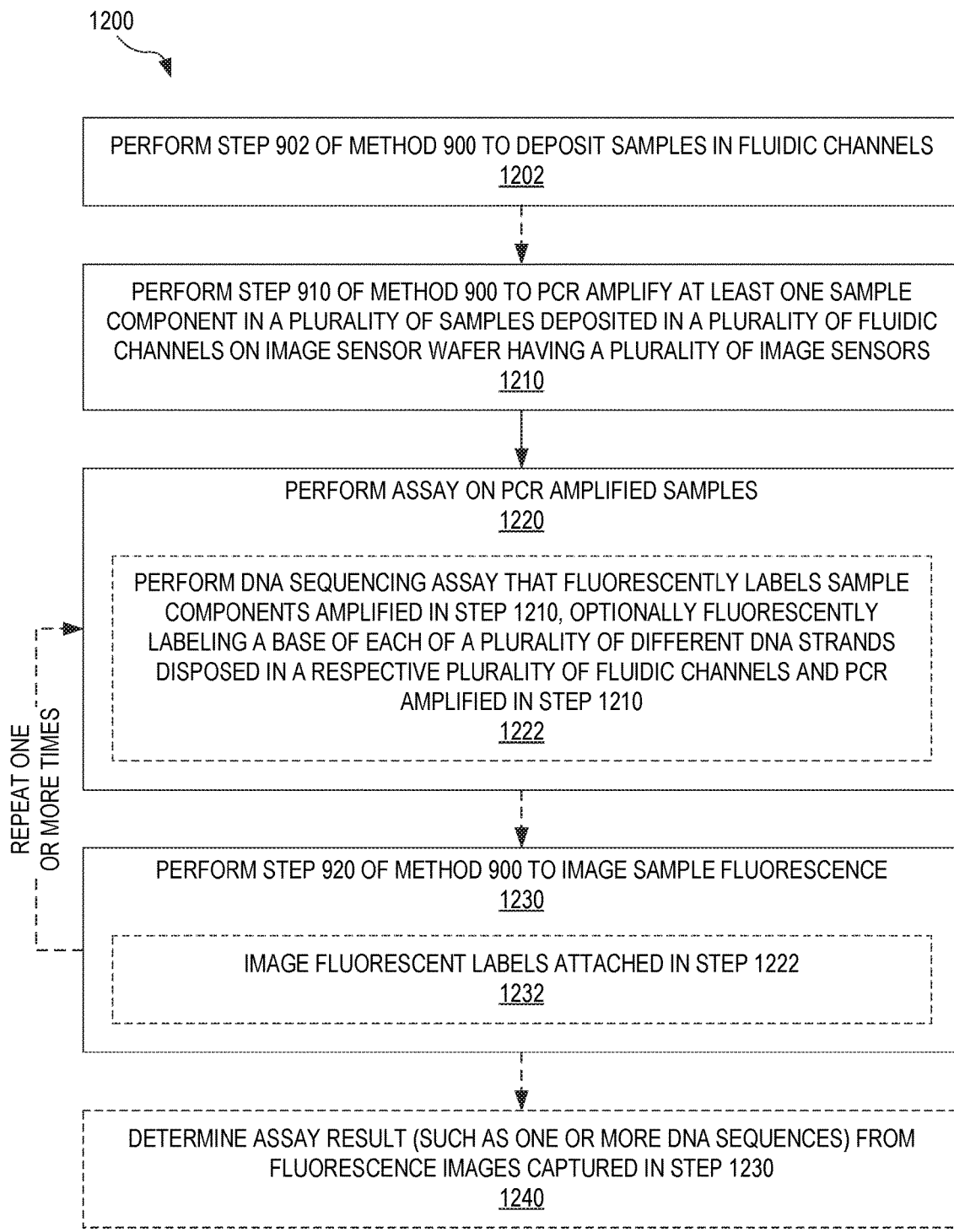
FIG. 12 illustrates a method for high-throughput, PCR amplification and fluorescence imaging readout of a plurality of samples, including post-PCR assay processing of amplified samples, according to an embodiment.

FIG. 12 illustrates one exemplary method 1200 for high-throughput, PCR amplification and fluorescence imaging readout of samples 150 including post-PCR assay processing of amplified samples 150, using high-throughput fluorescence imaging device 100 (FIG. 1). Method 1200 is an embodiment of method 200 (FIG. 2) and an extension of method 900 (FIG. 9). High-throughput fluorescence imaging system 800 (FIG. 8) may implement method 1200 as machine-readable instructions composed of protocol 818 and fluorescence image analysis instructions 832.

In a step 1202, method 1200 performs step 902 of method 900 to deposit samples 150 in fluidic channels 122, as discussed in reference to FIG. 9.

In a step 1210, method 1200 performs step 910 of method 900 to PCR amplify at least one component of samples 150, as discussed in reference to FIG. 9

In a step 1220, method 1200 further assays samples 150 PCR amplified in step 1210. Step 1220 includes, for example, adding reagents to fluidic channels 122, incubating samples 150 with such reagents, and/or modulating the temperature of samples 150 using heating module 130. In one example of step 1220, control module 810 executes protocol 818 to, through operation of fluidic module 860 and/or heating module 130, perform an assay.

In an embodiment, step 1220 includes a step 1222 of performing a DNA sequencing assay that fluorescently labels at least one base of a DNA strand included in samples 150 and amplified in step 1210. Step 1222 may utilize DNA sequencing methods known in the art. Optionally, step 1222 fluorescently labels a base of each of a plurality of different DNA strands respectively located in a plurality of fluidic channels 122 and PCR amplified in step 1210.

In a step 1230, method 1200 performs step 920 of method 900 to capture fluorescence images 170, as discussed in connection with FIG. 9. In an embodiment, step 1230 includes a step 1232, wherein high-throughput fluorescence imaging device 100 captures fluorescence images 170 of fluorescent labels attached in step 1222.

In certain embodiments, sequential steps 1222 and 1232 are performed repeatedly to sequence a plurality of DNA strands respectively disposed in a plurality of fluidic channels 122, wherein each repetition of steps 1222 and 1232 identifies one base of at least one of the plurality of DNA strands.

In an optional step 1240, fluorescence images 170 captured in step 1230 are analyzed to determine result 185, for example one or more DNA sequences. In one example of step 1240, processor 822 executes fluorescence image analysis instructions 832 to determine assay result 185.

Figure 13:
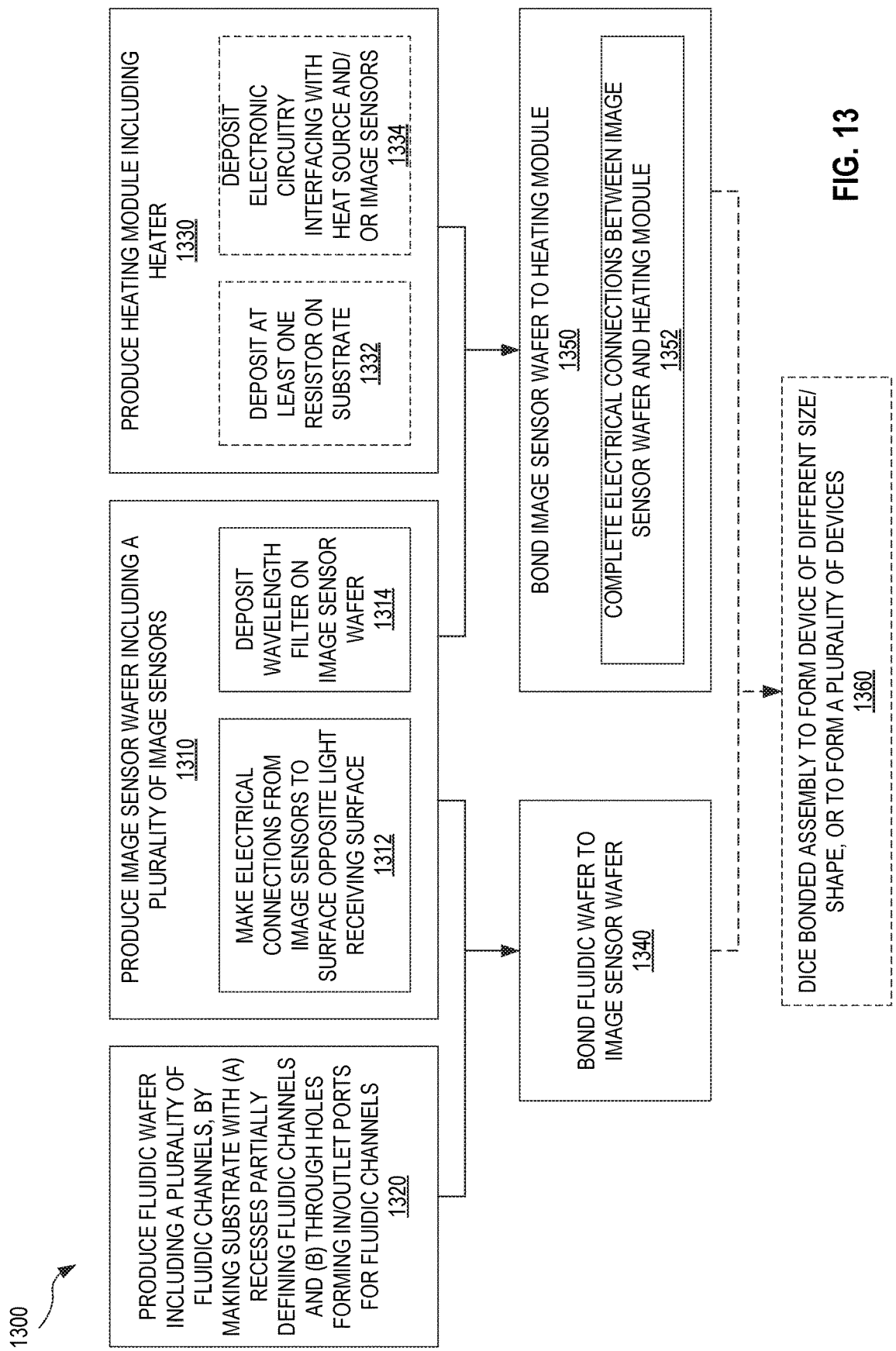
FIG. 13 illustrates a method for manufacturing the high-throughput fluorescence imaging device of FIG. 1, according to an embodiment.

FIG. 13 illustrates one exemplary method for manufacturing high-throughput fluorescence imaging device 100 (FIG. 1).

In a step 1310, method 1300 produces image sensor wafer 110, for example using CMOS manufacturing technology. Step 1310 includes steps 1312 and 1314. In step 1312, method 1300 makes electrical connections 514 (FIG. 5) and electrical connection pads 516 (FIG. 5), for example using CMOS manufacturing technology. Step 1312 is compatible at least with (a) image sensors 112 being front-side illuminated CMOS image sensors and (b) image sensors 112 being back-side illuminated CMOS image sensors. In step 1314, wavelength filter 316 is deposited on image sensor wafer 110, for example using methods known in the art such as photolithography, sputter coating, electron beam coating, and/or evaporative coating.

In a step 1320, method 1300 produces fluidic wafer 120, for example using CMOS manufacturing technology. Step 1320 includes making a substrate with (a) recesses capable of cooperating with light receiving surface 114 (or other planar surface) to form fluidic channels 122 and (b) through-holes forming fluidic ports 324 (FIG. 3) and 326 (FIG. 3) for each of fluidic channels 122. Step 1320 may form fluidic channels 122 and fluidic ports 324 and 326 with millimeter, micron, or sub-micron sized features.

In one embodiment, fluidic wafer 120 is integrally formed and step 1320 includes forming fluidic wafer 120 by etching and/or laser cutting, in a substrate such as a glass substrate, (a) recesses corresponding to fluidic channels 122 and (b) through-holes forming fluidic ports 324 and 326. In another embodiment, step 1320 forms fluidic wafer by bonding together two separate elements shown in FIG. 14.

Figure 14:
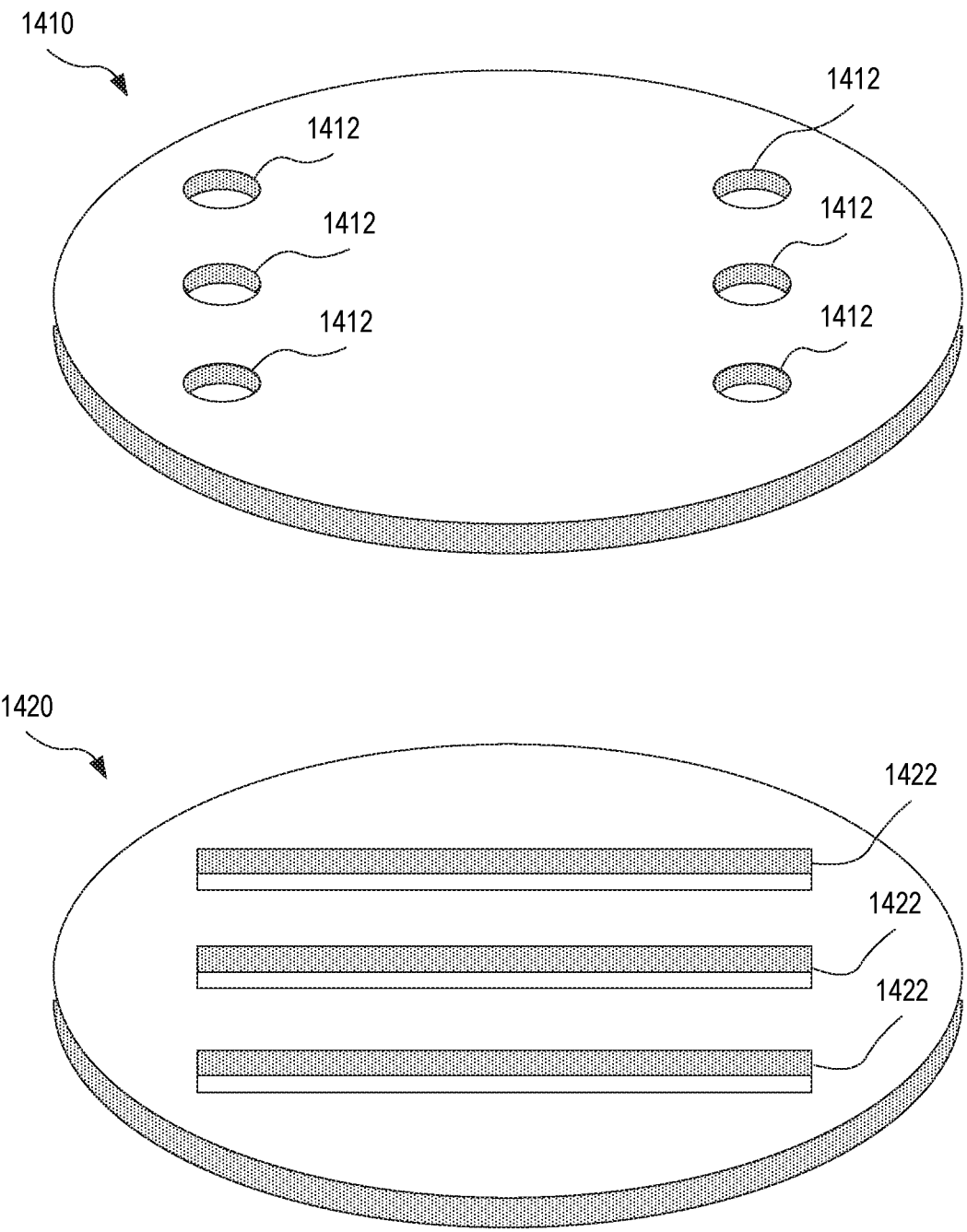
FIG. 14 illustrates a cover and a channel layer, according to an embodiment.

FIG. 14 illustrates one exemplary cover 1410 having a plurality of through-holes 1412 and one exemplary channel layer 1420 having a plurality of voids 1422 extending through the depth of channel layer 1420. Through-holes 1412 correspond to fluidic ports 324 and 326 and may be made, for example, by etching, drilling, or cutting. Voids 1422 correspond to the recesses that cooperate with light receiving surface 114 to form fluidic channels 122. Channel layer 1420 may be made from a pliable material, for example polydimethylsiloxane or a thin tape, by cutting voids in the pliable material. Alternatively, channel layer 1420 may be made through photolithography on a photoresist layer deposited either on the cover or on light receiving surface 114.

Cover 1410 may include a different number of through-holes 1412 and channel layer 1420 may include a different number of voids 1422 than illustrated in FIG. 14, without departing from the scope hereof. Also without departing from the scope hereof, cover 1410 and channel layer 1420 may have shape different from those shown in FIG. 14, and through-holes 1412 and voids 1422 may be located differently than illustrated in FIG. 14.

Again referring to FIG. 13, in a step 1330, method 1300 produces heating module 130 from a substrate. In an embodiment, step 1330 includes a step 1332 of depositing at least one resistor on the substrate to form resistive heat source 534 (FIG. 5), resistive heat source 634 (FIG. 6), or resistive heaters 734 (FIG. 7), using for example CMOS manufacturing technology. Optionally, step 1330 includes a step 1334 of depositing, on the substrate electronic circuitry that (a) interfaces with (a) heat source 334, to control heat generation by heat source 334 and/or (b) is configured to interface with electrical connection pads 516 (e.g., electrical connections 546).

In a step 1340, fluidic wafer 1340 is bonded to image sensor wafer 110. Step 1340 may use bonding methods known in the art including adhesive bonding (such as epoxy bonding), anodic bonding, direct bonding, and plasma activated bonding. In embodiments where step 1320 forms fluidic wafer 120 from separate channel layer 1420 and cover 1410, step 1340 may first bond channel layer 1420 to image sensor wafer 110, and next bond cover 1410 to channel layer 1420, without departing from the scope hereof.

In a step 1350, image sensor wafer 110 is bonded to heating module 130, for example using bonding methods known in the art including adhesive bonding (such as epoxy bonding), anodic bonding, direct bonding, and plasma activated bonding. Step 1350 includes a step 1352 of completing electrical connections between image sensor wafer 110 and heating module 130. Step 1352 may utilize reflow soldering or other soldering methods.

Steps 1340 and 1350 may be performed simultaneously, or sequentially in any order. In certain embodiments, method 1300 includes a step 1360 of dicing the assembly formed by steps 1310, 1320, 1330, 1340, and 1350 to form a high-throughput fluorescence imaging device 100 of a desired size and/or shape, or to form a plurality of high-throughput fluorescence imaging devices 100. Step 1360 may include completing electrical connections in areas not accessible prior to dicing.

Combinations of Features

Features described above as well as those claimed below may be combined in various ways without departing from the scope hereof. For example, it will be appreciated that aspects of one high-throughput fluorescence imaging system or device with sample heating capability, or associated method, described herein may incorporate or swap features of another high-throughput fluorescence imaging system or device with sample heating capability, or associated method, described herein. The following examples illustrate some possible, non-limiting combinations of embodiments described above. It should be clear that many other changes and modifications may be made to the methods and device herein without departing from the spirit and scope of this invention:

(A1) A high-throughput fluorescence imaging system with sample heating capability may include (a) an image sensor wafer having a plurality of image sensors for fluorescence imaging a plurality of samples disposed on the image sensor wafer and (b) a heating module, thermally coupled with the image sensor wafer, for heating the samples.

(A2) The high-throughput fluorescence imaging system denoted as (A1) may further include a plurality of fluidic channels for respectively containing the samples on the image sensor wafer.

(A3) In the high-throughput fluorescence imaging system denoted as (A2), the fluidic channels may be in contact with a light receiving surface of the image sensor wafer for lens-free imaging of the samples.

(A4) Each of the high-throughput fluorescence imaging systems denoted as (A2) and (A3) may further include a fluidic wafer having recesses that cooperate with the image sensor wafer to form the fluidic channels.

(A5) In each of the high-throughput fluorescence imaging systems denoted as (A2) through (A4), at least one of the fluidic channels may extend across several ones of the image sensors.

(A6) Each of the high-throughput fluorescence imaging systems denoted as (A1) through (A5) may further include a substrate incorporating the heating module.

(A7) In the high-throughput fluorescence imaging system denoted as (A6), the substrate may include (a) image readout contacts forming an interface for reading out fluorescence images captured by the image sensors.

(A8) In the high-throughput fluorescence imaging system denoted as (A7), the substrate may further include electrical connections for connecting the image sensors to the image readout contacts.

(A9) In each of the high-throughput fluorescence imaging systems denoted as (A1) through (A8), the heating module may include at least one resistor for resistively heating the image sensor wafer to heat the plurality of samples.

(A10) Each of the high-throughput fluorescence imaging systems denoted as (A1) through (A9) may further include a control module communicatively coupled with the image sensors and with the heating module, wherein the control module has machine-readable instructions that, when executed by a processor, effectuate at least one of (a) cycling of heat generation by the heating module to perform polymerase chain reaction amplification of one or more components of the samples and (b) fluorescence image capture by the image sensors to detect one or more products of the polymerase chain reaction amplification.

(A11) In each of the high-throughput fluorescence imaging systems denoted as (A1) through (A10), the image sensor wafer may include a wavelength filter, disposed between the plurality of fluidic channels and pixels of the plurality of image sensors, for at least partially blocking fluorescence excitation light.

(A12) In each of the high-throughput fluorescence imaging systems denoted as (A1) through (A11), the image sensors may be color sensitive for distinguishing between fluorescence emission of different wavelengths.

(B1) A method for high-throughput assay processing with fluorescence imaging readout may include (a) modulating temperature of a plurality of samples disposed in a respective plurality of fluidic channels on an image sensor wafer, including a plurality of image sensors, by heating the image sensor wafer using a heating module thermally coupled with the image sensor wafer, to control reaction dynamics in the samples, and (b) capturing a plurality of fluorescence images of the samples, using the plurality of image sensors, to detect one or more components of the plurality of samples.

(B2) In the method denoted as (B1), the step of capturing may include performing lens-free imaging of the plurality of samples to capture the plurality of fluorescence images.

(B3) In each of the methods denoted as (B1) and (B2), the step of modulating temperature may include cycling temperature of the image sensor wafer between a higher temperature range and a lower temperature range.

(B4) In the method denoted as (B3), the step of capturing may include capturing the plurality of fluorescence images while the image sensor wafer has temperature in the lower temperature range.

(B5) Each of the methods denoted as (B1) through (B4) may further comprising analyzing the plurality of fluorescence images to detect at least one product of polymerase chain reaction amplification of at least one component of the plurality of samples.

(B6) Each of the methods denoted as (B1) through (B5) may further include sequencing a plurality of deoxyribonucleic acid strands.

(B7) The method denoted as (B6) may include sequencing a plurality of deoxyribonucleic acid strands respectively included in the plurality of samples and respectively disposed in the plurality of fluidic channels.

(B8) Each of the methods denoted as (B6) and (B7) may further include attaching templates of the deoxyribonucleic acid strands to internal surfaces of the fluidic channels.

(C1) A method for manufacturing a high-throughput fluorescence imaging system with sample heating capability may include at least one of (a) bonding a fluidic wafer, including a plurality of fluidic channels, to an image sensor wafer including a plurality of image sensors, and (b) bonding a heating module, including a heater for generating heat, to the image sensor wafer to thermally couple the heater and the image sensor wafer.

(C2) The method denoted as (C1) may further include forming the plurality of fluidic channels by making recesses in the fluidic wafer, wherein the recesses together with the image sensor wafer define the plurality of fluidic channels at the interface between the fluidic wafer and the image sensor wafer.

(C3) Each of the methods denoted as (C2) and (C2) may further include forming electrical connections between the plurality of image sensors and image readout contacts on the heating module, wherein the image readout contacts form an interface for reading out fluorescence images captured by the plurality of image sensors.

(C4) Each of the methods denoted as (C1) through (C3) may further include depositing, on the image sensor wafer, a wavelength filter for at least partially blocking fluorescence excitation light.

(C5) Each of the methods denoted as (C1) through (C4) may further include depositing at least one resistor on a substrate to form the heating module.

Changes may be made in the above devices, systems and methods without departing from the scope hereof. It should thus be noted that the matter contained in the above description and shown in the accompanying drawings should be interpreted as illustrative and not in a limiting sense. The following claims are intended to cover generic and specific features described herein, as well as all statements of the scope of the present system and method, which, as a matter of language, might be said to fall therebetween.

What is claimed is:

1. A method for high-throughput assay processing with fluorescence imaging readout, comprising:

modulating temperature of a plurality of samples disposed in a respective plurality of fluidic channels on an image sensor wafer by heating the image sensor wafer using a heating module thermally coupled with the image sensor wafer, to control reaction dynamics in the samples, the fluidic channels being formed as respective recesses in a fluidic wafer disposed on a light-receiving surface of the image sensor wafer, the recesses being at the light-receiving surface, the image sensor wafer including a plurality of image sensors and being sandwiched between the fluidic wafer and the heating module; and capturing, via lens-free imaging, a plurality of fluorescence images of the samples, using the plurality of image sensors, to detect one or more components of the plurality of samples.

2. The method of claim 1, the step of modulating temperature comprising cycling temperature of the image sensor wafer between a higher temperature range and a lower temperature range; and the step of capturing comprising capturing the plurality of fluorescence images while the image sensor wafer has temperature in the lower temperature range.

3. The method of claim 2, further comprising analyzing the plurality of fluorescence images to detect at least one product of polymerase chain reaction amplification of at least one component of the plurality of samples.

4. The method of claim 3, further comprising sequencing a plurality of deoxyribonucleic acid strands respectively included in the plurality of samples and respectively disposed in the plurality of fluidic channels.

5. The method of claim 4, further comprising attaching templates of the deoxyribonucleic acid strands to internal surfaces of the fluidic channels.

6. The method of claim 1, at least one of the fluidic channels spanning over two or more of the image sensors.

7. The method of claim 1, the heating module being in direct contact with the image sensor wafer.

8. The method of claim 1, each of the image sensors including a rectangular array of photosensitive pixels.

9. The method of claim 8, the rectangular array including at least a million photosensitive pixels.

10. The method of claim 8, each of the image sensors being a non-zero distance away from each other one of the image sensors.

* * * * *